United States Patent [19]

Baron

[11] 4,300,542
[45] Nov. 17, 1981

[54] COMPRESSION DEVICE FOR HUMAN LIMBS

[76] Inventor: Howard C. Baron, 935 Park Ave., New York, N.Y. 10028

[21] Appl. No.: 104,187

[22] Filed: Dec. 17, 1979

[51] Int. Cl.³ .............................................. A61F 5/04
[52] U.S. Cl. ............................. 128/87 R; 128/89 R; 128/DIG. 20
[58] Field of Search ................... 128/89 R, 90, 87 R, 128/165, 166, DIG. 20

[56] References Cited

U.S. PATENT DOCUMENTS

| | | | |
|---|---|---|---|
| 3,373,741 | 3/1968 | Hill et al. | 128/90 |
| 3,375,822 | 4/1968 | Rose | 128/90 |
| 4,060,075 | 11/1977 | Blomer et al. | 128/90 |

Primary Examiner—John D. Yasko
Attorney, Agent, or Firm—Schulyer, Banner, Birch, McKie & Beckett

[57] ABSTRACT

A compression device for human limbs including a flexible sleeve and an expandible envelope which contains a pair of chemical agents which form a gas when mixed. In use, the chemical agents are mixed by manual manipulation of the expandible envelope, creating a gas which expands the envelope causing the envelope and the sleeve to bear against and to support an injured limb which has been inserted into the sleeve, thereby serving as a splint for broken bones or as a pressure dressing for the control of bleeding. The device may comprise a sleeve surrounding the injured limb and the envelope or, alternatively, a flexible panel forming a sleeve-like opening in which the limb is inserted.

9 Claims, 7 Drawing Figures

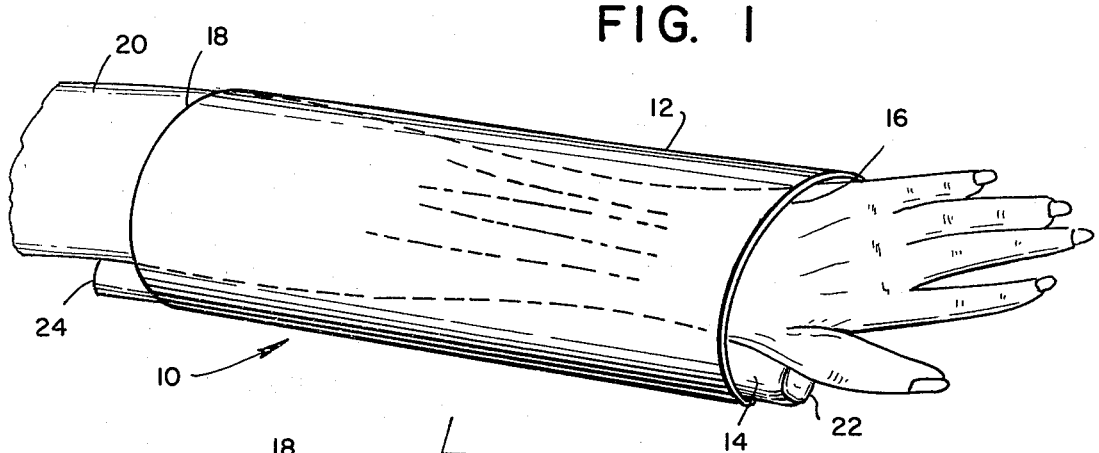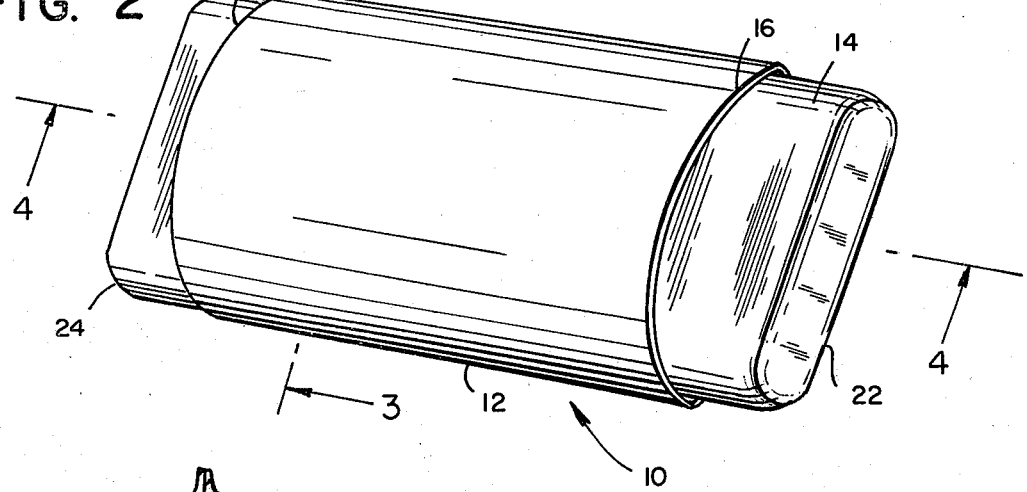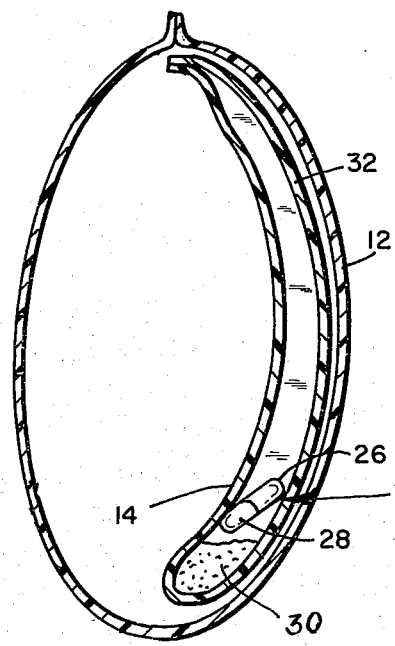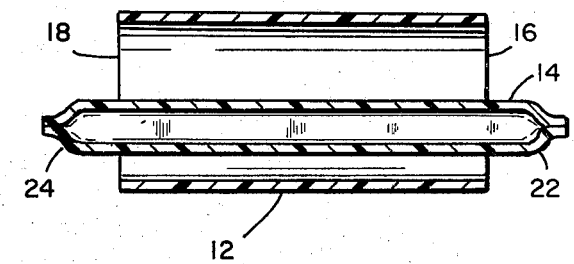

COMPRESSION DEVICE FOR HUMAN LIMBS

In the emergency treatment of traumatic injuries to human extremities, there has been a long felt need for a device which can be quickly and easily applied, preferably by the injured person himself, to stabilize the injured limb and to control bleeding.

With the current increased interest and participation in outdoor activities such as hiking, camping, mountain climbing and skiing, an increased number of persons engage in strenuous physical activity, under hazardous or semi-hazardous conditions, often in remote areas and often alone. In such activities it is not uncommon for a participant to sustain severe injuries to a limb. In the case of broken bones it is important to stabilize the limb, provide uniform support, and prevent flexure until medical attention can be obtained. Failure to do so often results in making the injury worse. In extreme cases the broken ends of the bones may even puncture the skin causing the fracture to become compound. The conventional first aid procedures require that a splint be obtained or fabricated from materials at hand and that the limb be immobilized by binding it to the splint. This procedure is often difficult to accomplish in remote areas due to the lack of suitable materials. Even if suitable materials are at hand, it is often impossible for an injured person, who is alone, to apply a splint due to the traumatic effects of his injury.

In the case of massive bleeding resulting from a cut or a laceration on a limb, the conventional first aid procedures require that the bleeding be controlled by application of direct pressure on the wound or, if the bleeding cannot be controlled by direct pressure, a tourniquet is applied to control the flow of blood to the limb. Both of these procedures have serious practical limitations. The self-application of a tourniquet if often difficult for an injured person to accomplish due to lack of suitable materials for construction of the tourniquet and the awkwardness and incapacity which results from the trauma of the injury. The application of direct pressure on the wound is usually difficult and sometimes impossible for an injured person to accomplish due to such factors as the awkward location of the wound or the inability to exert sufficient pressure to control the bleeding.

It is a major object of the present invention to provide a compression device for human limbs which can be easily applied, even by an injured person, to stabilize a broken limb and to control bleeding.

Another object of the present invention is to provide a compression device for human limbs which can be operated by just one hand.

Another object of the present invention is to provide a compression device for human limbs which is extremely light in weight and low in bulk, making it suitable for inclusion in portable first aid kits and for other applications where weight and space are at a premium.

Another object of the invention is the provision of a compression device for human limbs which is quickly and easily applied, yet is extremely effective in splinting fractured limbs as well as controlling severe bleeding. The compression device is particularly useful in mass diameter situations where a limited number of medical personnel is available for treating large numbers of injured persons.

Another object of the invention is to provide a compression device for human limbs which may be manufactured of clear plastic, thus making the injured area visually accessible.

Still another object of the invention is to provide a compression device for human limbs which comprises relatively few parts and which can be easily manufactured using mass production techniques, resulting in a relatively low unit cost.

In accordance with the present invention, the compression device for human limbs comprises an expandible envelope member and a sleeve member. The sleeve member is of a size which can easily fit around an arm or leg and encircle the expandible envelope. The expandible envelope contains a frangible container in the form of a capsule containing chemicals which, when mixed, will generate gas within the expandible envelope to inflate the envelope. The capsule may be grasped and squeezed through the walls of the expandible envelope to rupture the capsule and cause the chemicals to mix thereby generating gas. The expandible envelope in its initial flattened form occupies only a minor portion of the sleeve, but when it is inflated it occupies a major portion of the sleeve compressing the limb against the sleeve. The inflated envelope becomes rigid and cooperates with the sleeve to support and immobilize the limb. The expandible envelope may have ends which extend beyond the end of the sleeve to provide additional protection for the limb. The expandible envelope when inflated has the general form of a rectangular plate.

In an another embodiment the expandible envelope is made integral with the sleeve and when inflated has the general form of a curved plate.

Additional objects and advantages of the present invention will become apparent during the course of the following specification when taken in conjunction with the accompanying drawings, in which:

FIG. 1 is a perspective view of a compression device for human limbs made in accordance with the present invention, shown in use stabilizing a fracture of the radius and the ulna bones which are shown in broken lines on a fragmentary drawing of a forearm;

FIG. 2 is a perspective view of the compression device of FIG. 1 showing only the compression device and not the forearm;

FIG. 3 is a cross-sectional view taken along the line 3—3 of FIG. 2, showing the expandible envelope in a flattened state;

FIG. 4 is a cross-sectional view taken along the line 4—4 of FIG. 3, showing the expandible envelope inflated;

Figure 5:
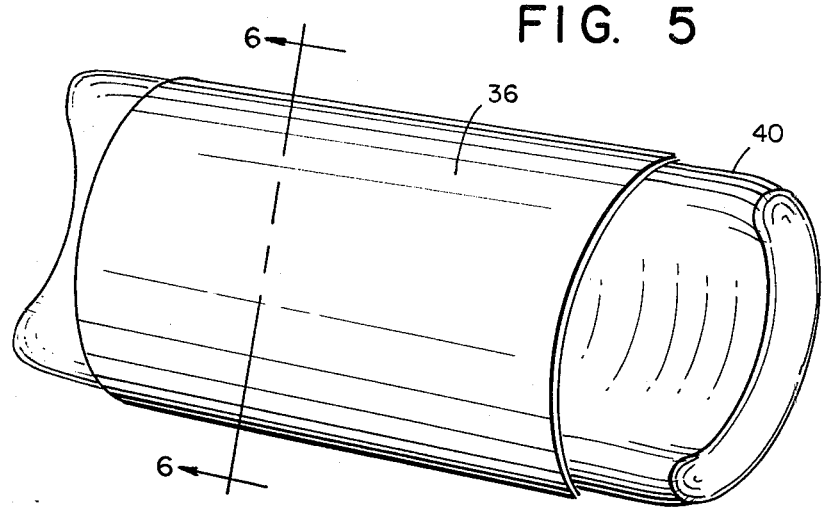
FIG. 5 is a perspective view similar to FIG. 2 showing a modified form of expandible envelope which is curved when inflated.

Referring in detail to the drawings, there is shown in FIGS. 1 to 4, by way of example, a compression device for human limbs 10 in accordance with the present invention, comprising a tubular sleeve member 12, an expandible envelope member 14, and a means 15 for generating gas to inflate the expandible envelope 14. The sleeve member 12 is made of a relatively soft bendable plastic such as transparent polyvinyl chloride, or the like. The sleeve member 12 has open ends 16 and 18 and is of a size so as to permit a human arm 20 or leg to be conveniently inserted therein.

The expandible envelope 14 is preferably made of the same soft and bendable plastic material as the sleeve 12, such as transparent polyvinyl chloride. The expandible envelope 14 is generally elongated in shape and is encircled by the sleeve 12. In the embodiment of the invention shown in FIGS. 1 to 4, the ends 22 and 24 of the envelope 14 project beyond the ends 16 and 18 respectively, of the sleeve 12.

In its initially flattened form, the envelope 14 occupies a minor portion of the sleeve 12 and does not interfere with the sleeve 12 being slipped onto an injured limb.

The gas generation means 15 may consist of a container of compressed gas which may be opened or ruptured to release gas within the envelope or, more preferably it may comprise a store of two or more chemicals which when mixed, generate gas. The expandible envelope 14, illustrated by way of example contains at least one thin walled capsule or ampoule 26 which may be ruptured or crushed to release a chemical agent 28 which then can mix with a chemical agent 30 which is stored within the expandible envelope 14.

Examples of suitable pairs of chemical agents for producing gas when mixed include a measured amount of baking soda in dry powder form stored in the envelope 14 and a supply of water stored in capsule 26. When the capsule 26 is ruptured, the water mixes with baking soda and generates carbon dioxide gas. As another example the capsule 26 may contain a supply of dilute hydrochloric acid and the envelope 14 may contain a supply of calcium carbonate.

Alternatively, the capsule 26 may comprise a thin walled capsule body having an integral transverse partition wall which is also thin and capable of being easily ruptured when the capsule is squeezed and crushed. At one side of the partition wall, the capsule may contain a measured supply of powdered chemical and at the other side of the partition wall the capsule may contain a supply of a liquid which will react with the powdered chemical to generate gas.

The transparent characteristics of the plastic material of the sleeve 12 and of the envelope 14 enable first aid personnel to easily monitor the condition of the injured limb. The transparency of the envelope 14 also makes it extremely simple for an operator to locate the capsule 26 in order to inflate the envelope 14.

When inflated, the expandible envelope 14 assumes the general shape of a thick rectangular plate as is shown in FIG. 2. The inflation of the envelope 14 makes the envelope relatively rigid and exerts a uniform pressure on a limb shown inserted in sleeve as is shown in FIG. 1. The device 10 conforms to the anatomical configuration of the limb and the limb is held securely between the sleeve 12 and the expanded envelope 14. The end portions 22, 24 of the envelope 14 which extend beyond the sleeve 12 provide additional stability and protection for the injured limb.

Medical personnel may easily remove the device 10 from a limb by merely cutting or puncturing the envelope 16, as with a knife or scissors. This causes the gas within the envelope 14 to escape to the atmosphere so that the envelope becomes deflated. The sleeve 12 may then be slipped off the limb for reuse with a new envelope, or alternatively, the sleeve may be easily cut away to expose the limb.

In FIG. 3 it will be seen that the sleeve 12 and the envelope 14 are each individually formed by heat sealing the marginal edges of the plastic film material. In an alternative construction, which is not shown, the wall 32 of the envelope 14 may be attached to the sleeve 12 using an appropriate technique such as a cement or a mechanical fastener.

Figure 6:
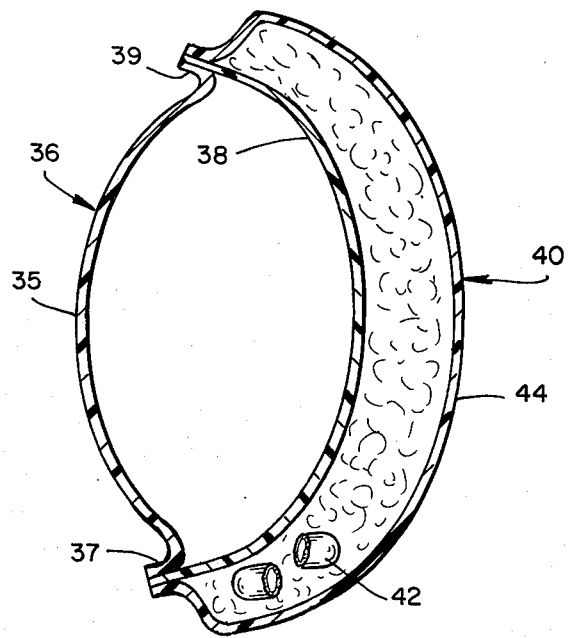
FIG. 6 is a cross-sectional view taken along the line 6—6 of FIG. 5.
Figure 7:
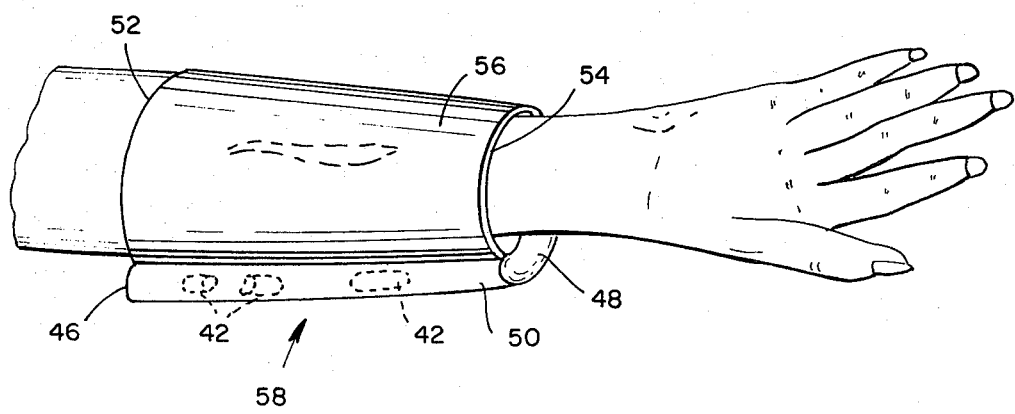
FIG. 7 is a perspective view of another modification of the compression device showing the device in use applying pressure to a wound.

FIGS. 5 to 7 show an alternative construction of the device 36 in which the sleeve member 36 is formed of a single panel 35 of bendable plastic film having edges 37, 39 which are attached by heat sealing to a wall 38 of the expandible envelope 40. Thus the wall 38 serves as both the inner wall of the envelope 40 and the inner wall of the sleeve member 36. Expandible envelope 40 contains gas generating means comprising a capsule 42 containing a store of liquid chemical and a store of a dry chemical as has been previously described. The panel which forms the outer wall 44 of the expandible envelope 40 is greater in width than the wall 38 so that when inflated, the expandible envelope 40 has the general form of a curved rectangular plate as is shown in FIGS. 5 and 6. This configuration of the expandible envelope 40 provides an additional measure of lateral support and lateral stability for the injured limb.

FIG. 7 shows another alternative construction of the device 50 similar to the construction of FIGS. 5 and 6 except that the ends 46 and 48 the expandible envelope 50 are generally in line with the ends 52 and 54 of the sleeve 56. The device 58 is shown in use applying pressure to a wound on a forearm 60. The sleeve 56 is transparent so that the wound may be continually inspected. In this alternative construction, the expandible envelope 50 may have a plurality of capsules each containing chemical agents for generating a gas as has been previously described. The pressure exerted on the wound may be increased during operation by rupturing additional capsules and generating additional quantities of gas. The inflation of the expandible envelope 50 creates a uniform pressure exerted on the limb which facilitates controlling the bleeding from the wound.

While preferred embodiments of the invention have been shown and described herein, it is obvious that numerous omissions, changes and additions may be made in such embodiments without departing from the spirit and scope of the invention.

What is claim:

1. A compression device for human limbs comprising an open ended tubular sleeve member having an interior space sized for receiving a human limb, an expandible envelope disposed within said tubular sleeve member at one side of said interior space and opposite to a wall portion of said sleeve member, with said human limb being receivable in said interior space between said expandible envelope and said wall portion, said expandible envelope having flexible walls, being completely sealed, and having a normal collapsed condition in which said expandible envelope occupies a minor portion of said interior portion of said interior space of said sleeve member, and means including a frangible member within said expandible envelope for rapidly generating a supply of substantially only gas therein, said frangible member being accessible from the exterior of said sleeve member, through said flexible walls of said expandible envelope, whereby said frangible member may be manually ruptured to rapidly generate gas within said expandible envelope, thereby causing said expandible envelope to expand rapidly without further manipulation thereof and press a limb inserted into said interior space against said wall portion of said sleeve member.

2. A compression device for human limbs according to claim 1 in which said expandible envelope is formed integrally with said sleeve member.

3. A compression device for human limbs according to claim 1 in which said expandible envelope has end portions which project beyond said sleeve member.

4. A compression device for human limbs according to claim 1 in which said expandible envelope when inflated forms a flat rectangular plate.

5. A compression device for human limbs according to claim 1 in which said expandible envelope when inflated forms a curved rectangular plate.

6. A compression device for human limbs according to claim 1 in which said sleeve member and said expandible envelope are made of flexible, transparent plastic sheet material.

7. A compression device for human limbs according to claim 1 in which said frangible member is a capsule containing a plurality of chemical ingredients capable of generating gas when mixed, said frangible member having at least one thin frangible partition wall separating said chemical ingredients.

8. A compression device for human limbs according to claim 1 in which said frangible member is a capsule containing a first chemical ingredient and with said expandible envelope containing a second chemical ingredient, with said first and said second chemical ingredients capable of generating gas when mixed.

9. A compression device for human limbs according to claim 7 in which said expandible envelope contains a plurality of said capsules.

* * * * *